United States Patent [19]

Alvarez

[11] 3,975,432

[45] Aug. 17, 1976

[54] PROCESS FOR PREPARING 2-(6-METHOXY-2-NAPHTHYL)PROPIONIC ACID

[75] Inventor: Francisco Alvarez, Sunnyvale, Calif.

[73] Assignee: Syntex Corporation, Panama City, Panama

[22] Filed: Feb. 21, 1974

[21] Appl. No.: 444,671

Related U.S. Application Data

[60] Continuation of Ser. No. 235,432, March 16, 1972, abandoned, which is a division of Ser. No. 95,377, Dec. 4, 1970, Pat. No. 3,663,584.

[52] U.S. Cl. .......................... 260/520 R; 260/429.9; 260/473 A
[51] Int. Cl.² ................... C07C 51/09; C07C 67/00
[58] Field of Search ....................... 260/520, 473 A

[56] References Cited
UNITED STATES PATENTS

| | | | |
|---|---|---|---|
| 3,658,858 | 4/1972 | Harrison | 260/520 X |
| 3,658,863 | 4/1972 | Harrison | 260/520 X |
| 3,663,584 | 5/1972 | Alvarez | 260/520 |

OTHER PUBLICATIONS

March "Advanced Organic Chemistry", McGraw Hill Book Co. (1968) pp. 353–354.

Gilman, *Organic Chemistry* vol. I, Wiley & Sons, Inc. (N.Y.) (1958) pp. 539–549.

Buehler et al., *Survey of Organic Synthesis*, Wiley–Interscience (NY) Dec. 11, 1970 pp. 22–29.

Shevendina et al. *The Organic Compounds of Zinc and Cadmium*, North–Holland Pub. Co. (1967) pp. 2, 73–78.

Shevendina et al., *Doklady Akad. Nauk. S.S.S.R.* 124 602–605 (1959).

Delarve C.A. 72 42721c.

*Primary Examiner*—Norman Morgenstern
*Attorney, Agent, or Firm*—Joseph I. Hirsch; William B. Walker

[57] ABSTRACT

2-(6-Methoxy-2-naphthyl)propionic acid is prepared by reacting di(6-methoxy-2-naphthyl)-zinc or 6-methoxy-2-naphthylzinc halide with a lower alkyl 2-halopropionate in a suitable solvent to form a lower alkyl 2-(6-methoxy-2-naphthyl)propionate and hydrolyzing the ester group thereof. The product has anti-inflammatory, analgesic and anti-pyretic activities.

10 Claims, No Drawings

PROCESS FOR PREPARING 2-(6-METHOXY-2-NAPHTHYL)PROPIONIC ACID

This is a continuation of application Ser. No. 235,432, filed Mar. 16, 1972, now abandoned, which, in turn, was a divisional application of application Ser. No. 95,377, filed Dec. 4, 1970, now U.S. Pat. No. 3,663,584.

This invention relates to a process for preparing 2-(6-methoxy-2-naphthyl)propionic acid and intermediates therefor.

In general, the process of this invention for preparing 2-(6-methoxy-2-naphthyl)propionic acid comprises the steps of reacting di-(6-methoxy-2-naphthyl)zinc or a 6-methoxy-2-naphthylzinc halide (bromide, iodide or chloride) with a lower alkyl 2-halopropionate (bromo, iodo or chloro) in an inert solvent until a lower alkyl 2-(6-methoxy-2-naphthyl)propionate is formed; hydrolyzing the ester group of the 2-(6-methoxy-2-naphthyl)-propionate; and recovering 2-(6-methoxy-2-naphthyl)propionic acid from the reaction mixture. Preferably, the product is resolved to yield a 2-(6-methoxy-2-naphthyl)propionic acid.

The process of this invention can be represented as follows:

Preferably the compounds of Formula I are reacted with at least one molar equivalent of a 2-halopropionate.

Suitable lower alkyl 2-halopropionates have, as the halo group, bromo, iodo or chloro and include methyl-2-bromopropionate, ethyl-2-bromopropionate, propyl-2-bromopropionate, isopropyl-2-bromopropionate, n-butyl-2-bromopropionate, t-butyl-2-bromopropionate, n-hexyl-2-bromopropionate, the corresponding iodo and chloro compounds, and the like.

Any conventional solvent which is inert to the reactants can be used in this reaction. Suitable solvents include hydrocarbon solvents such as benzene, toluene, xylene, cyclohexane, and ethers such as diethyl ether, other di(lower)alkyl ethers, tetrahydrofuran, tetrahydropyran, dimethoxyethane and the like.

The reaction is carried out at a temperature of from 0° to 80°C, preferably from 25° to 55°C. The time required for the reaction depends upon the reaction temperature, times of from 2 to 15 hours usually being sufficient.

The compounds of Formula III are then hydrolyzed to yield the compound of Formula IV. Hydrolysis can be achieved by treatment with base followed by acidification or by treatment with a strong acid. For basic

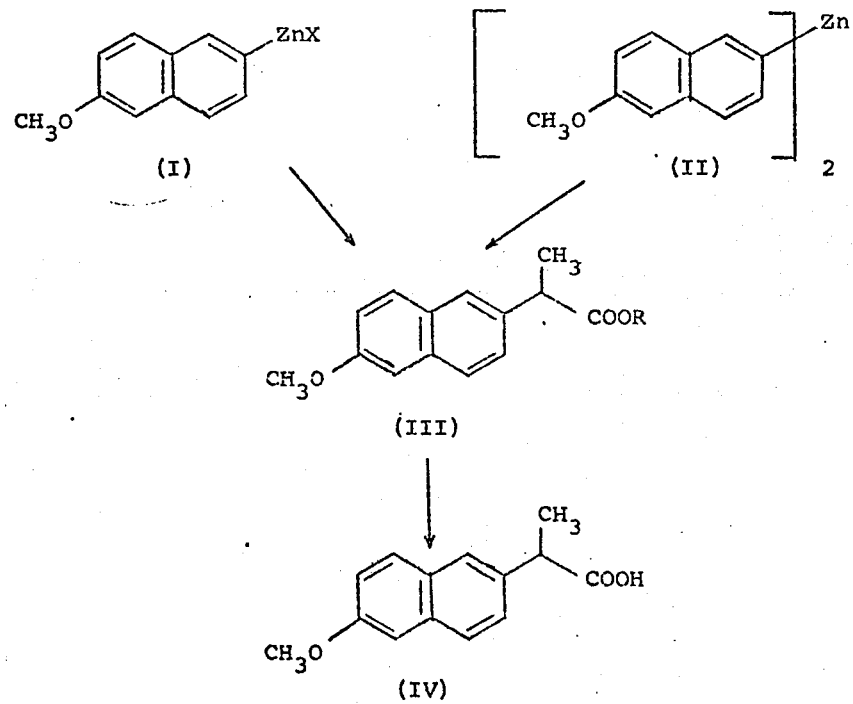

In the above formulas, R is a lower alkyl group and X is bromo, iodo or chloro.

The term "lower alkyl" includes primary, secondary and tertiary alkyl groups of straight and branched chain configuration having up to 6 carbons. Examples include methyl, ethyl, propyl, isopropyl, n-butyl, i-butyl, t-butyl, n-pentyl, n-hexyl and the like.

The compounds of Formula III are prepared by reacting the compounds of Formula I or the compound of Formula II, or mixtures thereof with a lower alkyl 2-halopropionate in an inert organic solvent until the corresponding lower alkyl 2-(6-methoxy-2-naphthyl)-propionate is formed.

hydrolysis, a solution of a strong base such as sodium or potassium hydroxide in a suitable solvent such as methanol is mixed with the reaction mixture, and the reaction mixture is maintained at a temperature of from 50°C to reflux temperature until hydrolysis occurs. Usually from 30 minutes to 2 hours is sufficient for this hydrolysis. The reaction mixture is then acidified with an acid such as acetic acid, trifluoroacetic acid, p-toluenesulfonic acid, hydrochloric acid, hydrobromic acid, hydroiodic acid, sulfuric acid, phosphoric acid and the like.

Alternatively, the reaction mixture is mixed with a solution of a strong organic or inorganic acid such as trifluroacetic acid, p-toluenesulfonic acid, hydrochloric acid, hydrobromic acid, hydroiodic acid, sulfuric acid, phosphoric acid and the like at a temperature of at least °C and preferably from 20°C to the reflux temperature of the mixture until the hydrolysis occurs. Suitable solvents for the acids include water, acetic acid, aqueous alcohols and the like. From 1 to 10 hours are usually sufficient for this hydrolysis. If acid hydrolysis is employed the free acid of Formula IV is formed directly. If necessary, the reaction mixture can be diluted with water to precipitate the product.

The product compound of Formula IV is then separated from the reaction mixture by conventional procedures. For example, the reaction mixture is filtered, mixed with water and acidified to precipitate the compound of Formula IV. The precipitate can be removed by filtration and recrystallized from acetone-hexane. Alternatively, the reaction mixture can be extracted with a suitable solvent such as methylene chloride or diethyl ether, the organic phase separated and evaporated, and the residue recrystallized from acetone-hexane. Chromatography can also be used to purify and/or isolate the product compound of Formula IV.

The preferred product is d 2-(6-methoxy-2-naphthyl)propionic acid. The optical resolution of the compound of Formula IV can be achieved by selective biological degradation or by preparation of diastereo isomer salts of the 2-(6-methoxy-2-naphthyl)propionic acid with a resolved optically active amine base such as cinchonidine and then separating the thus formed diastereo isomer salts by fractional crystallization. The separated diastereo isomer salts are then acid cleaved to yield the respective d 2-(6-methoxy-2-naphthyl)propionic acid.

The compounds of Formulas I and II can be prepared from 6-methoxy-2-naphthylbromide, chloride or iodide by a procedure which can be represented as follows:

in a suitable solvent such as hydrocarbon solvent at elevated temperatures. Whether the compound of Formula I or the compound of Formula II are formed depends upon the amount of zinc halide employed in the reaction, one molar equivalent of the zinc compound yielding primarily the compound of Formula I, and one-half molar equivalent yielding the compound of Formula II. By choice of from 0.5 to 1 molar equivalent of zinc halide, mixtures of the compounds of Formula I and II can be obtained, if desired.

The compound of Formula IV exhibits anti-inflammatory, analgesic and anti-pyretic activities and is accordingly useful for the treatment of inflammation, pain and pyrexia in mammals. For example, inflammatory conditions of the muscular skeletal system, skeletal joints and other tissues can be treated. Accordingly, this compound is useful in the treatment of conditions characterized by inflammation such as rheumatism, concussion, laceration, arthritis, bone fractures, post-traumatic conditions and gout.

This invention is further illustrated by the following specific but non-limiting examples.

EXAMPLE 1

A solution of 11.3 g. of 2-bromo-6-methoxynaphthalene in 30 ml. of benzene is slowly added to 1.2 g. of magnesium turnings in 20 ml. of benzene at reflux temperature under nitrogen.

The resulting solution of 6-methoxy-2-naphthylmagnesium bromide in 50 ml. of benzene under nitrogen is added 3.14 g. of anhydrous zinc chloride. The temperature of the mixture is maintained at a temperature of from 25°–30°C for 1 hour, yielding a solution of di-(6-methoxy-2-naphthyl)zinc.

To this solution is added 9.96 g. of ethyl 2-bromopropionate in 5 ml. of anhydrous benzene. The temperature of the reaction mixture is maintained at from 50°

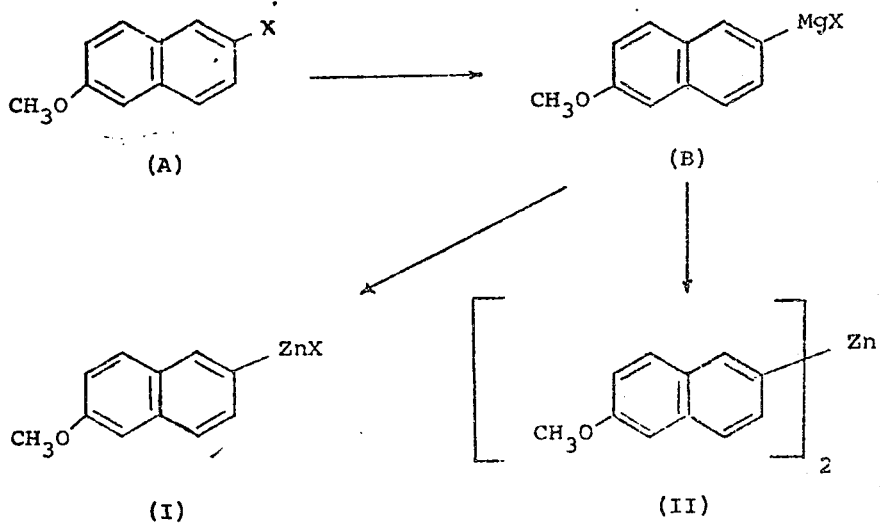

In the above formulas, X is as previously defined.

The compounds of Formula A are all known compounds. The compounds of Formula B can be prepared by reacting the compounds of Formula A with mmagnesium in a suitable organic solvent such as an ether solvent, e.g. tetrahydrofuran, at elevated temperatures. The compounds of Formulas I and II are prepared by reacting the compounds of Formula B with zinc halide to 55°C for 15 hours, under nitrogen, and then the reaction mixture is mixed with 175 ml. of a 1.5 N hydrochloric acid solution, followed by 65 ml. of methylene chloride. The mixture is filtered, and the organic phase is separated. The aqueous acid layer is extracted with two further 30 ml. quantities of methylene chloride, and the methylene chloride extracts are combined, washed with 50 ml. of water, and stripped of solvents under vacuum to yield ethyl 2-(6-methoxy-2-naphthyl)propionate.

A solution of 6.0 g. of potassium hydroxide, 6 ml. of water and 60 ml. of methanol is added to the ethyl 2-(6-methoxy-2-naphthyl)propionate, and the mixture is heated at reflux for 45 minutes, cooled to ambient temperature, acidified and mixed with 60 ml. of water. Methanol is removed by evaporation in vacuo, and the resultant solution is extracted with two 60 ml. portions of methylene chloride. The combined methylene chloride extracts are evaporated to dryness to yield 2-(6-methoxy-2-naphthyl)propionic acid.

EXAMPLE 2

A solution of dl 2(6-methoxy-2-naphthyl)propionic acid in methanol is prepared by dissolving 230 g. of the product of Example 1 in 4.6 l. of warm methanol. The resulting solution is boiled until it becomes turbid; then sufficient methanol is added to make the solution clear again. This hot solution is added to a solution of 296 g. of cinchonidine and 74 l. of methanol heated to about 60°C. The solutions are combined while stirring, and the combined mixture is then allowed to reach room temperature over a 2 hour period. After the reaction mixture has reached room temperature, it is stirred for an additional 2hours and then filtered. The filtered solids are washed with several portions of cold methanol and dried.

100 Grams of the cinchonidine salt crystals are added to a stirred mixture of 600 ml. of ethyl acetate and 450 ml. of a 2 N aqueous hydrochloric acid solution. After the mixture has been stirred for 2 hours, the ethyl acetate layer is removed and washed to neutrality, dried over sodium sulfate and evaporated to yield d 2-(6-methoxy-2-naphthyl)propionic acid.

I claim:

1. A process for preparing 2-(6-methoxy-2-naphthyl)propionic acid comprising the steps of:

a. reacting di-(6-methoxy-2-naphthyl)zinc or 6-methoxy-2-naphthylzinc halide wherein the halide is a chloride, bromide or iodide, with a lower alkyl 2-halopropionate wherein the halo group is a chloro, iodo or bromo group, in an inert organic solvent until a lower alkyl 2-(6-methoxy-2-naphthyl)propionate is formed;

b. hydrolyzing the ester group of the 2-(6-methoxy-2-naphthyl)propionate; and c. recovering 2-(6-methoxy-2-naphthyl)propionic acid from the reaction mixture.

2. The process of claim 1 wherein the lower alkyl 2-halopropionate is a lower alkyl 2-bromopropionate.

3. The process of claim 1 wherein 2-(6-methoxy-2-naphthyl)propionic acid is resolved to yield d 2-(6-methoxy-2-naphthyl)propionic acid.

4. The process of claim 1 wherein di-(6-methoxy-2-naphthyl)zinc is reacted with said lower alkyl 2-halopropionate.

5. The process of claim 1 wherein 6-methoxy-2-naphthylzinc halide is reacted with said lower alkyl 2-halopropionate.

6. The process of claim 1 wherein said lower alkyl 2-halopropionate is ethyl-2-bromopropionate.

7. The process of claim 1 wherein di-(6-methoxy-2-naphthyl)zinc is reacted with ethyl-2-bromopropionate to afford ethyl-2-(6-methoxy-2-naphthyl)propionate.

8. The process of claim 1 wherein said di-(6-methoxy-2-naphthyl)zinc or 6-methoxy-2-naphthylzinc halide is reacted with said lower alkyl 2-halopropionate at about 0°–80°C for about 2–15 hours.

9. The process of claim 8 wherein said lower alkyl 2-halopropionate is ethyl 2-bromopropionate.

10. The process of claim 8 wherein di-(6-methoxy-2-naphthyl)zinc is reacted with ethyl 2-bromopropionate in Step (a) to afford ethyl 2-(6-methoxy-2-naphthyl)propionate.

* * * * *